United States Patent
Sakurada

(10) Patent No.: US 9,782,067 B2
(45) Date of Patent: Oct. 10, 2017

(54) OPTOMETRIC APPARATUS

(71) Applicant: TOPCON CORPORATION, Itabashi-ku (JP)

(72) Inventor: Tomohiro Sakurada, Itabashi-ku (JP)

(73) Assignee: TOPCON CORPORATION, Itabashi-ku (JP)

( * ) Notice: Subject to any disclaimer, the term of this patent is extended or adjusted under 35 U.S.C. 154(b) by 10 days.

(21) Appl. No.: 15/131,383

(22) Filed: Apr. 18, 2016

(65) Prior Publication Data
US 2016/0345824 A1    Dec. 1, 2016

(30) Foreign Application Priority Data
May 29, 2015  (JP) .................... 2015-109435

(51) Int. Cl.
| | | |
|---|---|---|
| *A61B 3/10* | (2006.01) | |
| *A61B 3/103* | (2006.01) | |
| *A61B 3/032* | (2006.01) | |
| *A61B 3/028* | (2006.01) | |
| *A61B 3/00* | (2006.01) | |

(52) U.S. Cl.
CPC ............ *A61B 3/103* (2013.01); *A61B 3/0025* (2013.01); *A61B 3/0075* (2013.01); *A61B 3/0285* (2013.01); *A61B 3/032* (2013.01)

(58) Field of Classification Search
CPC ....... A61B 3/103; A61B 3/032; A61B 3/0285; A61B 3/0075; A61B 3/0025
USPC ................................ 351/205–246
See application file for complete search history.

(56) References Cited

U.S. PATENT DOCUMENTS

2006/0139573 A1   6/2006  Sakurada

FOREIGN PATENT DOCUMENTS

JP        2006-181271        7/2006

*Primary Examiner* — Jack Dinh
(74) *Attorney, Agent, or Firm* — Oblon, McClelland, Maier & Neustadt, L.L.P.

(57) ABSTRACT

According to one embodiment, an optometric apparatus includes a movement mechanism system and left and right optometry units. The movement mechanism system is suspended from an arm. The left and right optometry units are configured to be moved by the movement mechanism system. The left and right optometry units each include an optical element applying part, a target presenting part, and an objective measurement part. The optical element applying part is configured to selectively apply a plurality of optical elements to a subject's eye. The target presenting part is configured to selectively present a plurality of visual targets to the subject's eye. The objective measurement part is configured for performing objective refraction measurement of the subject's eye.

9 Claims, 6 Drawing Sheets

OPTOMETRIC APPARATUS

CROSS-REFERENCE TO RELATED APPLICATION

This application is based upon and claims the benefit of priority from Japanese Patent Applications No. 2015-109435, filed 29 May 2015; the entire contents of which are incorporated herein by reference.

FIELD

Embodiments described herein relate generally to an optometric apparatus.

BACKGROUND

The optometric apparatus is an ophthalmologic apparatus for testing the sight, the visual function, or the like by presenting a visual target to the subject's eye through an optical element.

Among such optometric apparatuses is the one capable of testing the subject's eye by a combination of subjective measurement and objective measurement. For example, Japanese Unexamined Patent Application Publication 2006-181271 discloses an optometric apparatus that includes a pedestal, a drive mechanism box arranged on the pedestal, a pair of left and right optical heads with a built-in measurement optical system, and a face rest for fixing the face of a subject during a test.

Since the conventional optometric apparatus is placed on the pedestal when used to measure the subject's eye, it occupies the pedestal.

In a general subjective measurement, the examiner presents a visual target to the subject's eye and conducts a test based on a response to the visual target from the subject while observing his/her expression and the like to improve the accuracy of the test. However, with the conventional optometric apparatus, a test is performed in a state where the subject places his/her face against the face rest. As a result, the examiner cannot observe facial expressions of the subject during a test.

SUMMARY

Embodiments are intended to provide an optometric apparatus enabling the observation of facial expressions and the like of the subject during subjective measurement and objective measurement as well as achieving space saving.

According to one aspect of an embodiment, an optometric apparatus includes a movement mechanism system and left and right optometry units. The movement mechanism system is suspended from an arm. The left and right optometry units are configured to be moved by the movement mechanism system. The left and right optometry units each include an optical element applying part, a target presenting part, and an objective measurement part. The optical element applying part is configured to selectively apply a plurality of optical elements to a subject's eye. The target presenting part is configured to selectively present a plurality of visual targets to the subject's eye. The objective measurement part is configured for performing objective refraction measurement of the subject's eye.

DETAILED DESCRIPTION

An optometric apparatus according to an exemplary embodiment is described in detail below with reference to the drawings.

<Configuration>

Figure 1:
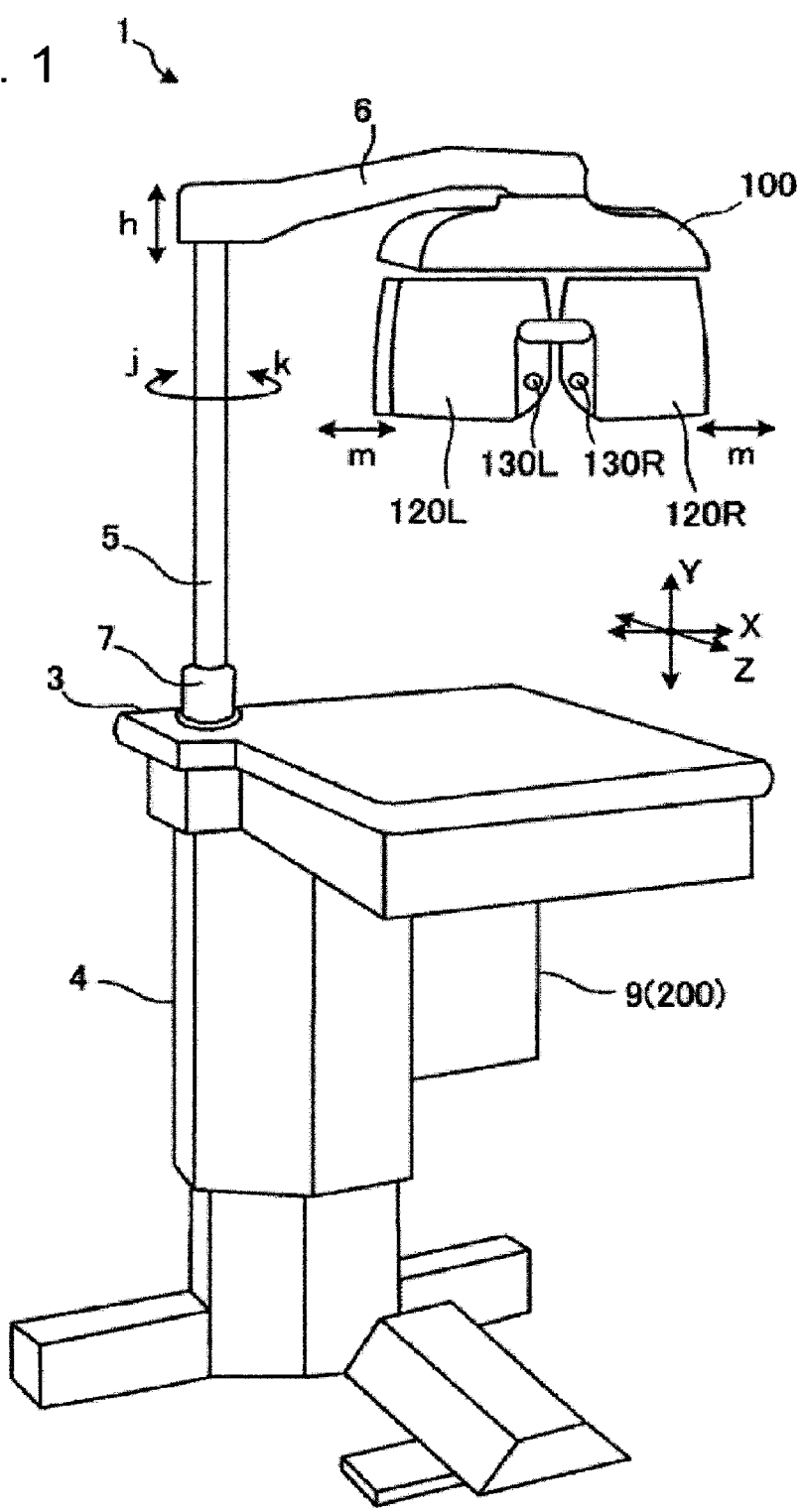
FIG. 1 is a schematic diagram illustrating the exterior configuration of an optometric apparatus according to an embodiment.

FIG. 1 schematically illustrates the external configuration of an optometric apparatus 1 according to an embodiment. The optometric apparatus 1 of the embodiment can be communicably connected to an examiner controller (e.g., tablet terminal), a subject controller (e.g., a control lever unit), and the like (not illustrated) via a wired or wireless communication path. The optometric apparatus 1 is controlled based on an operation performed on the examiner controller, the subject controller, and the like. In the following, the lateral and vertical directions as viewed from the subject may be sometimes referred to as X direction and Y direction, respectively, and the depth direction (front-back direction) of a measuring head 100 as viewed from the subject may be sometimes referred to as Z direction.

The optometric apparatus (ophthalmologic apparatus) 1 includes a measuring head (also called a refractor or a phoropter) 100 and a control device 200. The optometric apparatus 1 is capable of performing subjective measurement and objective measurement. In the subjective measurement, a visual target is presented to the eye of a subject (subject's eye) to obtain information about the subject's eye based on a response to the visual target from the subject. In the objective measurement, information about the subject's eye is obtained mainly through a physical method without reference to a response from the subject.

The optometric apparatus 1 is provided with an optometry table 3. The optometry table 3 is used to support the measuring head 100 and place the examiner controller, the subject controller, or the like. The optometry table 3 is placed on the floor as being supported by a support portion 4. The height of the optometry table 3 is adjustable up and down.

A post 5 stands upwards from the optometry table 3. The post 5 holds the base end portion of a horizontal arm 6 at its end portion. The measuring head 100 is suspended at the end portion of the horizontal arm 6. For example, the post 5 can be rotated around the axis (in directions indicated by arrows j and k) by an arm movement mechanism 7. Thus, the horizontal arm 6 is rotated around the axis. In other words, the measuring head 100 is rotated around the axis. Accordingly, the measuring head 100 can be retracted from an examination space above the optometry table 3. Thus, a test can be carried out efficiently by using the empty space above the optometry table 3.

The arm movement mechanism 7 may be configured to move the end portion of the post 5 in the vertical direction (direction indicated by arrow h) as an arm vertical movement mechanism. Thereby, the horizontal arm 6 is moved in the vertical direction. In other words, the measuring head 100 is moved in the vertical direction. The arm movement mechanism 7 may also be configured to move the horizontal arm 6 in the vertical direction by extending and contracting the post 5, which projects upward from the optometry table 3. The arm movement mechanism 7 serves as an arm extending and contracting mechanism. In this case also, the measuring head 100 can be retracted from the examination space above the optometry table 3.

Incidentally, a table or the like for storing the measuring head 100 may be provided separately so that the measuring head 100 can be positioned stably by the aforementioned rotation, the vertical movement, or the like. In this case, it is possible to reduce the continued load on the horizontal arm 6 due to the weight of the measuring head 100.

The arm movement mechanism 7 can be operated by an operator to manually move the horizontal arm 6 around the axis and in the vertical direction. The arm movement mechanism 7 may be configured to move the horizontal arm 6 by an electric mechanism. In this case, the optometric apparatus 1 further includes an actuator that generates a driving force for moving the arm movement mechanism 7 and a transmission mechanism that transmits the driving force. The actuator is formed of, for example, a pulse motor. The transmission mechanism is formed of, for example, a combination of gears or a rack-and-pinion.

A housing 9 is provided on the side of the support portion 4 to store the control device 200 and the like. The structure of the optometry table 3 is not limited to that illustrated in FIG. 1.

<Measuring Head>

The measuring head 100 includes a left-eye optometry unit 120L and a right-eye optometry unit 120R. The left-eye optometry unit 120L and the right-eye optometry unit 120R are provided with optometry windows 130L and 130R, respectively. The left eye of the subject (subject's left eye) is tested through the optometry window 130L. The right eye of the subject (subject's right eye) is tested through the optometry window 130R.

Figure 2:
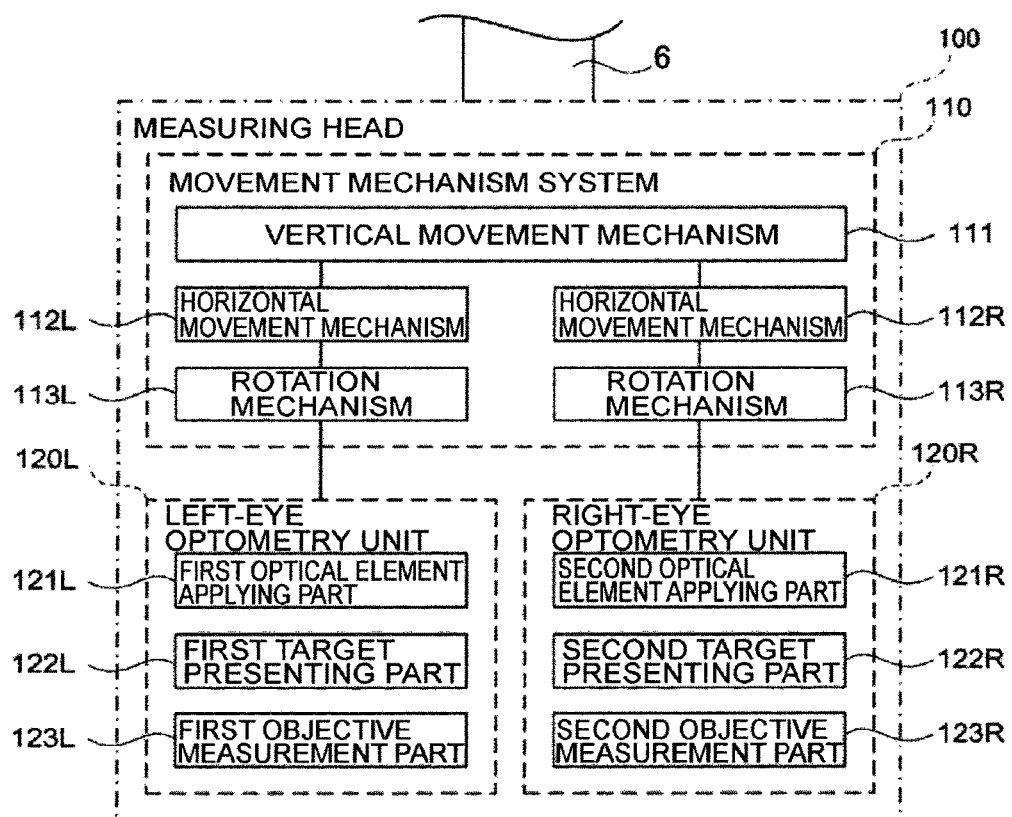
FIG. 2 is a schematic diagram illustrating the configuration of the optometric apparatus of the embodiment.
Figure 3:
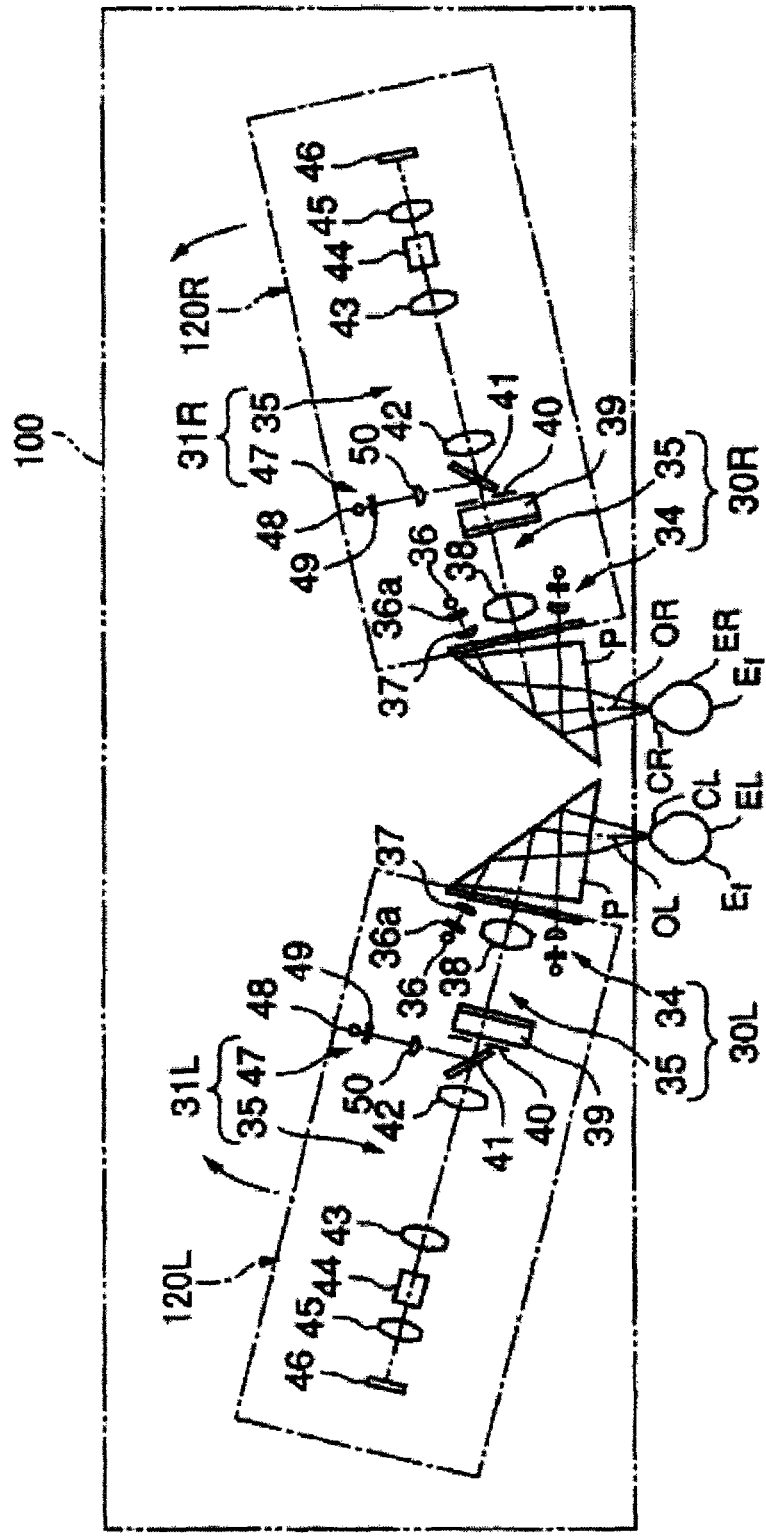
FIG. 3 is a schematic diagram illustrating the configuration of an optical system of the optometric apparatus of the embodiment.

FIGS. 2 and 3 are block diagrams illustrating an example of the configuration of the measuring head 100 of the embodiment. The measuring head 100 includes a movement mechanism system 110, the left-eye optometry unit 120L, and the right-eye optometry unit 120R. The movement mechanism system 110 is suspended from the horizontal arm 6. The movement mechanism system 110 three-dimensionally moves the left-eye optometry unit 120L and the right-eye optometry unit 120R independently of each other or in conjunction with each other. The left-eye optometry unit 120L accommodates an optical system for the test of the left eye of the subject (subject's left eye). The right-eye optometry unit 120R accommodates an optical system for the test of the right eye of the subject (subject's right eye).

<Movement Mechanism System>

The movement mechanism system 110 includes a vertical movement mechanism 111, horizontal movement mechanisms 112L and 112R, and rotation mechanisms 113L and 113R. The movement mechanism system 110 may further include the arm movement mechanism 7.

The vertical movement mechanism 111 is configured to move the horizontal movement mechanisms 112L and 112R, the rotation mechanisms 113L and 113R, the left-eye optometry unit 120L, and the right-eye optometry unit 120R in the vertical direction (Y direction). Thereby, the positions of the optometry windows 130L and 130R in the height direction can be adjusted according to the positions of the subject's eyes. The vertical movement mechanism 111 has a known configuration including, for example, a pulse motor and a feed screw, and moves the horizontal movement mechanism 112L and the like in the vertical direction in response to a control signal from the control device 200. Incidentally, the vertical movement mechanism 111 may be configured to move the horizontal movement mechanism 112L and the like in the vertical direction in response to an operation performed by the operator.

The horizontal movement mechanism 112L is configured to move the rotation mechanism 113L and the left-eye optometry unit 120L in the horizontal direction, i.e., in the lateral direction (X direction) and the front-back direction (Z direction). The horizontal movement mechanism 112L has a known configuration using, for example, a pulse motor and a feed screw, and moves the rotation mechanism 113L and the left-eye optometry unit 120L in the horizontal direction in response to a control signal from the control device 200. Incidentally, the horizontal movement mechanism 112L may be configured to move the rotation mechanism 113L and the like in the horizontal direction in response to an operation performed by the operator.

The horizontal movement mechanism 112R is configured to move the rotation mechanism 113R and the right-eye optometry unit 120R in the horizontal direction. The horizontal movement mechanism 112R may be configured to move the rotation mechanism 113R and the like in conjunction with the movement of the horizontal movement mechanism 112L, or move the rotation mechanism 113R and the like independently of the movement of the horizontal movement mechanism 112L. The horizontal movement mechanism 112R has a known configuration as with the horizontal movement mechanism 112L, and moves the rotation mechanism 113R and the right-eye optometry unit 120R in the horizontal direction in response to a control signal from the control device 200. Incidentally, the horizontal movement mechanism 112R may be configured to move the rotation mechanism 113R and the like in the horizontal direction in response to an operation performed by the operator.

The distance between the left-eye optometry unit 120L and the right-eye optometry unit 120R can be changed by moving the rotation mechanisms 113L and 113R, and the like using the horizontal movement mechanisms 112L and 112R. Thereby, it is possible to change the distance between the left-eye optometry unit 120L and the right-eye optometry unit 120R according to the interpupillary distance of the subject. The left-eye optometry unit 120L or the right-eye optometry unit 120R can be moved in the front-back direction (Z direction) of the measuring head 100 as viewed from the subject.

The rotation mechanism 113L is configured to rotate the left-eye optometry unit 120L around a predetermined first axis. The rotation mechanism 113L has a known configuration using, for example, a pulse motor and a rotating shaft, and rotates the left-eye optometry unit 120L around the first axis in response to a control signal from the control device 200. Incidentally, the rotation mechanism 113L may be configured to rotate the left-eye optometry unit 120L around the first axis in response to an operation performed by the operator.

The rotation mechanism 113R is configured to rotate the right-eye optometry unit 120R around a predetermined second axis. The second axis is arranged in a position separated from the first axis by a predetermined distance. The distance between the first axis and the second axis may be adjustable. The rotation mechanism 113R may rotate the right-eye optometry unit 120R in conjunction with the rotation of the rotation mechanism 113L, or rotate the right-eye optometry unit 120R independently of the rotation of the rotation mechanism 113L. The rotation mechanism 113R has a known configuration as with the rotation mechanism 113L, and rotates the right-eye optometry unit 120R around the second axis in response to a control signal from the control device 200. Incidentally, the rotation mechanism 113R may be configured to rotate the right-eye optometry unit 120R around the second axis in response to an operation performed by the operator.

The rotation mechanisms 113L and 113R respectively rotate the left-eye optometry unit 120L and the right-eye optometry unit 120R to thereby relatively change the orientation of the left-eye optometry unit 120L and that of the right-eye optometry unit 120R. In one example, the left-eye optometry unit 120L and the right-eye optometry unit 120R are rotated in the opposite directions around the eyeball rotation points of the subject's left eye and the subject's right eye respectively. With this, the subject's eyes can be converged and diverged.

<Configuration of Each Optometry Unit>

The left-eye optometry unit 120L and the right-eye optometry unit 120R can be controlled individually.

The left-eye optometry unit 120L includes a first optical element applying part 121L, a first target presenting part 122L, and a first objective measurement part 123L. The first optical element applying part 121L is configured to selectively apply a plurality of optical elements to the subject's left eye. The first target presenting part 122L is configured to selectively present a plurality of visual targets to the subject's left eye. The first objective measurement part 123L is used for the objective refraction measurement of the subject's left eye.

The right-eye optometry unit 120R includes a second optical element applying part 121R, a second target presenting part 122R, and a second objective measurement part 123R. The second optical element applying part 121R is configured to selectively apply a plurality of optical elements to the subject's right eye. The second target presenting part 122R is configured to selectively present a plurality of visual targets to the subject's right eye. The second objective measurement part 123R is used for the objective refraction measurement of the subject's right eye.

<Optical Element Applying Part>

The first optical element applying part 121L and the second optical element applying part 121R each include a plurality of optical elements and a drive mechanism.

The optical elements of each optometry unit are a set of various lenses for testing the visual function of a subject's eye. The optical elements include at least one of, for example, a spherical lens, a cylindrical lens, a progressive lens, and a prism lens. The optical elements are grouped for each type of optometric parameters.

The optometric parameters indicate the test conditions for testing the visual function of the subject's eye. Examples of the types of the optometric parameters include at least one of spherical power, cylindrical power, astigmatic axis angle, additional power, interpupillary distance, prism power, and prism direction. As an example of grouping according to the types of the optometric parameters, a group of spherical power includes a plurality of spherical lenses each having a different spherical power. A group of cylindrical power includes a plurality of cylindrical lenses each having a different cylindrical power. Incidentally, the group of cylindrical power may be further divided into groups for each astigmatic axis angle. A group of additional power includes a plurality of progressive lenses each having a different diopter power. A group of prism power includes a plurality of prism lenses each having a different prism power. Incidentally, the group of prism power may be further divided into groups for each prism direction. The interpupillary distance is a test condition that is set according to the distance between the pupils of the subject's eyes. The interpupillary distance is set by sliding one or both of the left-eye optometry unit 120L and the right-eye optometry unit 120R in the horizontal direction (direction indicated by arrow m in FIG. 1).

The drive mechanism that includes each optometry unit is configured such that each of the optical elements can be arranged in and retracted from the optometry window. For example, the drive mechanism includes a plurality of turret plates each having a circular shape. In the drive mechanism, each of the turret plates is configured to be rotatable about the center of the circle as its rotation axis around the circumference. Each of the turret plates has a plurality of holes near the circumference edge. The optical elements are fitted in the holes. The drive mechanism rotates the turret plates to thereby position/retract each of the optical elements in/from the optometry window.

Each of the first optical element applying part 121L and the second optical element applying part 121R switches the optical elements in response to a control signal from the control device 200. With this, it is possible to selectively apply, to the subject's eye, at least one of the spherical power, cylindrical power, astigmatic axis angle, additional power, interpupillary distance, prism power, and prism direction.

<Target Presenting Part, Objective Measurement Part>

Figure 4:
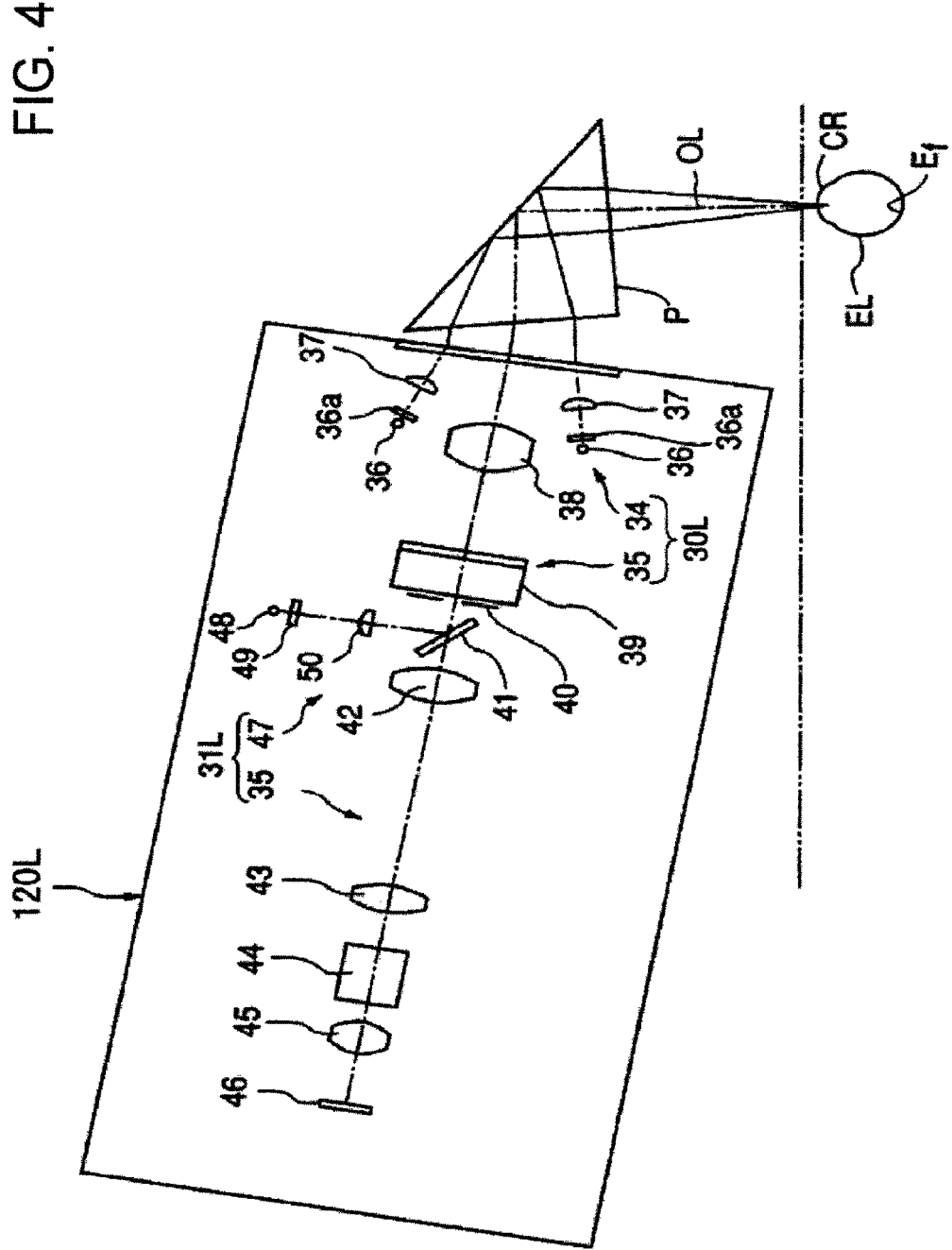
FIG. 4 is a schematic diagram illustrating the configuration of the optical system of the optometric apparatus of the embodiment.
Figure 5:
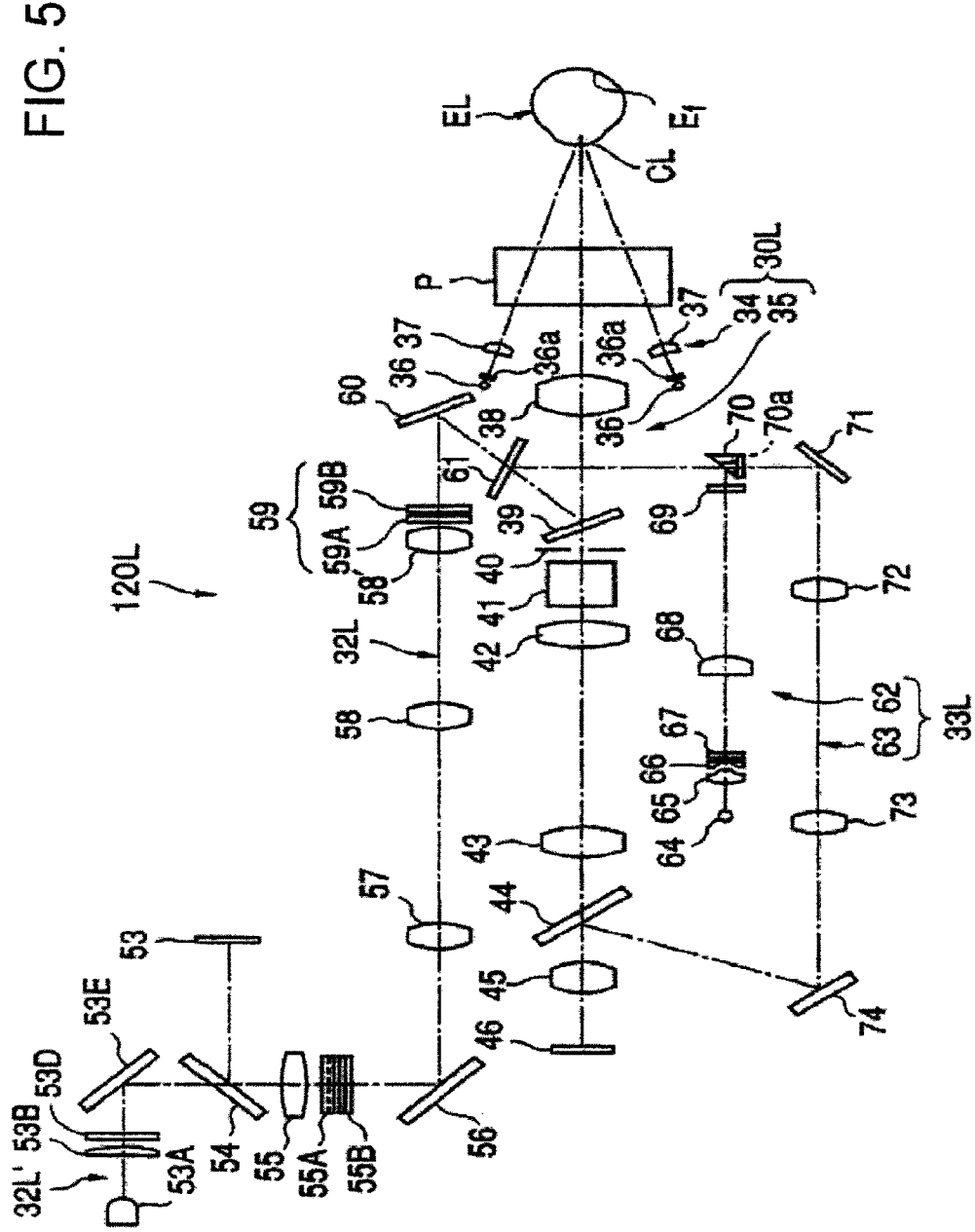
FIG. 5 is a schematic diagram illustrating the configuration of the optical system of the optometric apparatus of the embodiment.

The left-eye optometry unit 120L and the right-eye optometry unit 120R each include an optical system as illustrated in FIGS. 3 to 5. The left-eye optometry unit 120L and the right-eye optometry unit 120R are configured to perform the measurement of the both eyes of the subject by the operation of the optical systems. The measurement includes subjective refraction measurement performed by using the target presenting part and the objective refraction measurement performed by using the objective measurement part. The examiner or the subject operates the controller as appropriate to conduct a test.

<Configuration of the Optical System>

With reference to FIGS. 3 to 5, a detailed description is given of the configuration of the measurement optical systems in the left-eye optometry unit 120L and the right-eye optometry unit 120R. FIGS. 3 to 5 illustrate the case where the optical elements are not applied to the subject's eyes by the optical element applying part. The optical elements that can be applied to the subject's eye by means of the optical element applying part are not illustrated in FIGS. 3 to 5.

As illustrated in FIGS. 3 to 5, the left-eye optometry unit 120L, which performs the measurement of the subject's left eye EL, includes an anterior eye segment imaging optical system 30L, an XY alignment optical system 31L, a target projection optical system 32L, and a refractive power measurement optical system 33L. Similarly, the right-eye optometry unit 120R, which performs the measurement of the subject's right eye ER, includes an anterior eye segment imaging optical system 30R, an XY alignment optical system 31R, a target projection optical system, and a refractive power measurement optical system (see FIG. 3). The measurement optical system of the left-eye optometry unit 120L and that of the right-eye optometry unit 120R are configured to be bilaterally symmetrical. Accordingly, the measurement optical system of only one of them, the left-eye optometry unit 120L, is described below unless otherwise specified.

The anterior eye segment imaging optical system 30L provided in the left-eye optometry unit 120L includes an anterior segment illumination optical system 34 and an imaging optical system 35.

As illustrated in FIGS. 4 and 5, the anterior segment illumination optical system 34 includes a light source 36, an aperture 36a, and a projection lens 37. The light source 36 is used to illuminate the anterior segment of the subject's left eye EL. The aperture 36a restricts the cross-sectional area of a light beam emitted from the light source 36. The projection lens 37 projects the light beam having passed through the aperture 36a onto the anterior segment of the subject's left eye EL.

The imaging optical system 35 includes a prism P, an objective lens 38, a dichroic mirror 39, an aperture 40, a dichroic mirror 41, relay lenses 42 and 43, a dichroic mirror 44, and a CCD lens 45. After having illuminated the anterior segment of the subject's left eye EL, the light from the anterior segment illumination optical system 34 is reflected by the anterior eye segment, and the reflected light is incident on the prism P. The light beam reflected by the reflecting surface of the prism P is incident on the objective lens 38. The CCD lens 45 forms an image of the light beam on the light receiving surface of CCD 46.

The XY alignment optical system 31L is an optical system for aligning the optical system of the left-eye optometry unit 120L in the XY direction with respect to the subject's left eye EL. The XY alignment optical system 31L includes an alignment illumination optical system 47 and the imaging optical system 35. The alignment illumination optical system 47 projects a light beam for alignment to the subject's left eye EL. The imaging optical system 35 receives the light beam for alignment projected to the subject's left eye EL and reflected therefrom as an alignment light receiving optical system.

As illustrated in FIGS. 3 and 4, the alignment illumination optical system 47 includes an illumination light source 48, an aperture 49 as an alignment target, a relay lens 50, the dichroic mirror 41, the aperture 40, the dichroic mirror 39, the objective lens 38, and the prism P. The illumination light source 48 emits a light beam for alignment in the XY direction.

The target projection optical system 32L includes a liquid crystal display (LCD) 53, a half mirror 54, a collimator lens 55, rotary prisms 55A and 55B, a reflecting mirror 56, a movable lens 57, relay lenses 58 and 58', a variable cross cylinder (VCC) lens 59, a reflecting mirror 60, dichroic mirrors 61 and 39, the objective lens 38, and the prism P. The LCD 53 displays a variety of visual targets (charts) for optometry. The half mirror 54 reflects light from the LCD 53. The rotary prisms 55A and 55B are used to adjust the prism power and prism base direction in a phoria test. The movable lens 57 is used to perform fixation and fogging of the subject's left eye EL, for example. The VCC lens 59 is used to adjust the astigmatic power and the astigmatic axis angle of the subject's left eye EL in the cross cylinder test.

Visual targets are selectively displayed on the LCD 53. Examples of the visual targets include a fixation target constituted of a landscape chart, a visual acuity chart such as a Landolt ring or the like for vision test, a cross cylinder test chart, a radiation chart for astigmatism test, a cross chart for phoria test, and a red green test chart. Incidentally, the LCD 53 may be replaced by a known visual target presenting means that presents a visual target by illuminating, from the rear, a turret plate having a plurality of visual targets formed thereon.

The rotary prisms 55A and 55B are driven to be rotated independently by a pulse motor or the like. When the rotary prisms 55A and 55B are rotated in opposite directions, the prism power is continuously changed. When the rotary prisms 55A and 55B are rotated integrally in the same direction, the prism base direction is continuously changed.

The VCC lens 59 includes a cylindrical lens 59A having a convex surface (positive power) and a cylindrical lens 59B having a concave surface (negative power). The cylindrical lenses 59A and 59B are driven by a driving device such as a pulse motor, and rotated independently about the optical axis of the target projection optical system 32L. When the cylindrical lenses 59A and 59B are rotated in opposite directions, the astigmatic power is changed. When the cylindrical lenses 59A and 59B are rotated integrally in the same direction, the astigmatic axis angle is changed.

The movable lens 57 is driven by a driving device such as a pulse motor, and moved in the optical axis direction of the target projection optical system 32L to thereby change the spherical power to be applied to the subject's left eye EL. For example, the movable lens 57 is moved in the optical axis direction by an amount corresponding to the refractive power of the subject's left eye EL to perform fixation and fogging of the subject's left eye EL.

As illustrated in FIG. 5, a fusion target projection optical system 32L' is arranged in the transmission direction of the half mirror 54 of the target projection optical system 32L. The fusion target projection optical system 32L' includes a light emitting diode (LED) 53A that emits illumination light, a collimator lens 53B, a fusion frame chart 53D, and a total reflection mirror 53E. The fusion frame chart 53D is formed of, for example, a light shielding member having a square transmission window (fusion frame). Besides, the collimator lens 53B is provided with a diffusing surface, and is configured to diffuses light from the LED 53A to thereby uniformly illuminate the fusion frame chart 53D.

Although, in this embodiment, the fusion target projection optical system 32L' is provided independently of the target projection optical system 32L, a fusion frame may be displayed on the LCD 53.

As illustrated in FIG. 5, the refractive power measurement optical system 33L includes a measurement light beam projection optical system 62 configured to project a light beam for objective measurement onto the subject's left eye EL, and a measurement light beam receiving optical system 63 configured to receive the light projected onto the subject's left eye EL and reflected therefrom.

The measurement light beam projection optical system 62 includes a measurement light source 64 such as an infrared LED, a collimator lens 65, a conical prism 66, a ring target 67, a relay lens 68, an annular aperture 69, a perforated prism 70 having a through hole 70a formed in the center, the dichroic mirrors 61 and 39, the objective lens 38, and the prism P.

The measurement light beam receiving optical system 63 includes the prism P, on which the light reflected from the fundus Ef of the subject's left eye EL is incident, the objective lens 38, the dichroic mirrors 39 and 61, the through hole 70a of the perforated prism 70, a reflecting mirror 71, a relay lens 72, a movable lens 73, a reflecting mirror 74, the dichroic mirror 44, the CCD lens 45, and the CCD 46.

Under the control of the control system (described later), the measuring head 100 is configured to automatically perform the alignment of the optical system of each of the left-eye optometry unit 120L and the right-eye optometry unit 120R, objective optometry measurement, subjective optometry measurement, and the like. The measuring head 100 may also be configured to automatically perform a binocular balance test. In the subjective optometry measurement, a value obtained by an objective optometry measurement (objective value) is utilized. In particular, in a cross cylinder test among subjective optometry measurements, the astigmatic power and the astigmatic axis angle obtained by an objective optometry measurement are used.

<Control System>

Figure 6:
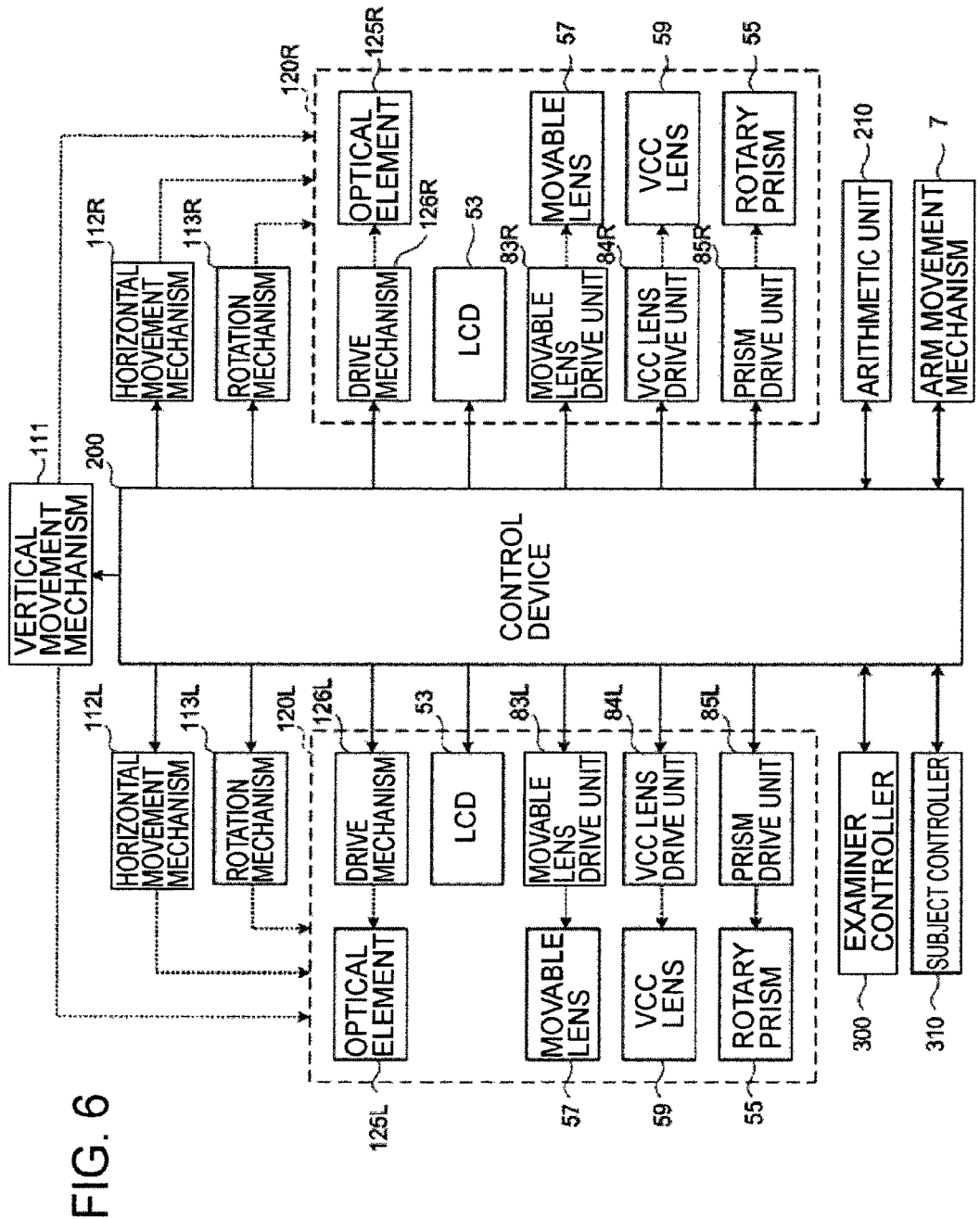
FIG. 6 is a schematic diagram illustrating the configuration of a control system of the optometric apparatus of the embodiment.

Referring to FIG. 6, a description is given of a control system of the optometric apparatus 1 of the embodiment. FIG. 6 is a block diagram schematically illustrating the configuration of the main part of the control system of the optometric apparatus 1. In FIG. 6, like reference numerals designate like parts as in FIGS. 1 to 5, and the same description may not be repeated.

As illustrated in FIG. 6, the control device 200 for controlling each unit of the apparatus is the center of the control system of the optometric apparatus 1. The control device 200 is, for example, stored in the housing 9. The control device 200 includes a nonvolatile storage device, such as a read-only memory (ROM), which stores a computer program for optometry including a control program to perform a process as described later, and an arithmetic control processor, such as a central processing unit (CPU), which executes the computer program.

A computer device (not illustrated) may be connected to the optometric apparatus 1. In this case, the computer device is used as a console of the optometric apparatus 1. In addition, the computer device is also used to store and manage test results obtained by the optometric apparatus 1. Besides, the CPU, the storage device, or the like of the computer device may be configured as a component of the control device 200.

The control device 200 controls the operation of the left-eye optometry unit 120L and the right-eye optometry unit 120R. Specifically, the control device 200 controls the vertical movement mechanism 111 for vertically moving the left-eye optometry unit 120L and the right-eye optometry unit 120R. The control device 200 controls the horizontal movement mechanism 112L for horizontally moving the left-eye optometry unit 120L as well as the rotation mechanism 113L for rotating the left-eye optometry unit 120L. Similarly, the control device 200 controls the horizontal movement mechanism 112R for horizontally moving the right-eye optometry unit 120R as well as the rotation mechanism 113R for rotating the right-eye optometry unit 120R. The control device 200 may be configured to control the arm movement mechanism 7 for vertically moving or rotating the horizontal arm 6.

The control device 200 also controls the operation of the optical systems stored in the left-eye optometry unit 120L and the right-eye optometry unit 120R. The control device 200 performs, for example, the control of a drive mechanism 126L for selectively applying optical elements 125L to the subject's left eye EL, the control of a drive mechanism 126R for selectively applying optical elements 125R to the subject's right eye ER, and the like. Further, the control device 200 performs the display control of the LCD 53, the operation control of movable lens drive units 83L and 83R for driving the movable lens 57 in the optical axis direction, and the like. The control device 200 further performs the operation control of VCC lens drive units 84L and 84R for rotating the VCC lens 59 about the optical axes of the target projection optical systems 32L and 32R respectively, the operation control of prism drive units 85L and 85R for rotating the rotary prisms 55A and 55B about the optical axes respectively, and the like.

The control device 200 controls an arithmetic unit 210. The arithmetic unit 210 obtains an objective value based on a measurement result obtained by objective refraction measurement using the left-eye optometry unit 120L or the right-eye optometry unit 120R. For example, the measurement light beam projection optical system 62 projects a ring-shaped measurement light beam onto the fundus Ef. The measurement light beam reflected from the fundus Ef is received by the CCD 46. The arithmetic unit 210 may analyze the shape of an image (ring visual target image) of the light beam reflected from the fundus obtained by the CCD 46 in a known manner to obtain the objective value. The arithmetic unit 210 may be included in the control device 200.

In addition to examples of the control operation as described above, the control device 200 controls the on/off operation of the light source 36, the illumination light source 48, the LED 53A, and the like. The control device 200 may execute any data processing and any operation control of the optometric apparatus 1.

The each optometry unit may include a light source for keratometry. The light source for keratometry emits a ring-shaped light beam. The ring-shaped light beam is projected onto the cornea of the subject's eye. The CCD 46 receives the ring-shaped light beam reflected from the cornea. The arithmetic unit 210 performs a predetermined calculation on an image of the cornea reflection light beam obtained by the CCD 46, thereby calculating a parameter representing the shape of the cornea as the objective value.

The control device 200 can be connected to an examiner controller 300 and a subject controller 310 via a wired or wireless communication path. In response to an operation signal corresponding to the operation performed on the examiner controller 300 or the subject controller 310, the control device 200 controls corresponding units of the optometric apparatus 1. The control device 200 is capable of displaying operation screens, various types of information for performing measurements, and the like on the display of the examiner controller 300 and the subject controller 310.

The operation principle of alignment using the optical system described above, the principle of subjective measurement, the principle of objective measurement, the principle of the corneal shape measurement, and the like are already known. Therefore, they are not described in detail here.

The function of the first optical element applying part 121L is implemented by the optical elements 125L and the drive mechanism 126L. The function of the second optical element applying part 121R is implemented by the optical elements 125R and the drive mechanism 126R.

The function of the first target presenting part 122L is implemented by the target projection optical system 32L included in the left-eye optometry unit 120L. The function of the second target presenting part 122R is implemented by the target projection optical system 32R included in the right-eye optometry unit 120R.

The function of the first objective measurement part 123L is implemented by the refractive power measurement optical system 33L included in the left-eye optometry unit 120L. The function of the second objective measurement part 123R is implemented by a refractive power measurement optical system 33R included in the right-eye optometry unit 120R.

The rotation mechanisms 113L and 113R are an example of the "first mechanism" according to the embodiment. The horizontal movement mechanisms 112L and 112R are an example of the "second mechanism" of the embodiment. The vertical movement mechanism 111 is an example of the "third mechanism" of the embodiment. The arm movement mechanism 7 is an example of the "fourth mechanism", the "arm vertical movement mechanism", or the "arm extending and contracting mechanism" of the embodiment. The control device 200 is an example of the "controller" of the embodiment.

<Effects>

Described below are the effects of the optometric apparatus according to the embodiment.

According to the embodiment, the optometric apparatus (e.g., the optometric apparatus 1) includes a movement mechanism system (e.g., the movement mechanism system 110), and left and right optometry units (e.g., the left-eye optometry unit 120L and the right-eye optometry unit 120R). The movement mechanism system is suspended from an arm (e.g., the horizontal arm 6). The left and right optometry units are moved by the movement mechanism system. Each of the left and right optometry units includes an optical element applying part (e.g., the first optical element applying part 121L, the second optical element applying part 121R), a target presenting part (e.g., the first target presenting part 122L, the second target presenting part 122R), and an objective measurement part (e.g., the first objective measurement part 123L, the second objective measurement part 123R). The optical element applying part is configured to selectively apply a plurality of optical elements (e.g., the optical elements 125L, 125R) to a subject's eye (e.g., the subject's left eye EL, the subject's right eye ER). The target presenting part is configured to selectively present a plurality of visual targets to the subject's eye. The objective measurement part is configured for performing objective refraction measurement of the subject's eye.

With this configuration, each of the left and right optometry units includes the optical element applying part, the target presenting part, and the objective measurement part, and is movable by the movement mechanism system. Thereby, the optometric apparatus is capable of performing objective measurement and subjective measurement, while achieving space saving. Besides, the left and right optometry units can be moved by the movement mechanism system that is suspended from the arm. As a result, the examiner can perform a subjective measurement while observing the expression of the subject (nose, mouth, cheeks, etc.) and the like. Thus, it is possible to improve the accuracy of the subjective measurement. For example, the optometric apparatus may be separately provided with an image pickup device for photographing the expression of the subject who is undergoing a subjective measurement or an objective measurement using the optometry unit to thereby obtain an image of the subject.

In the optometric apparatus of the embodiment, the movement mechanism system may include a first mechanism (e.g., the rotation mechanism 113L, the rotation mechanism 113R) configured to relatively change the orientations of the left and right optometry units.

With this configuration, a test can be performed while the subject's eyes are converged by the first mechanism.

Further, in the optometric apparatus of the embodiment, the movement mechanism system may include a second mechanism (e.g., the horizontal movement mechanism 112L, the horizontal movement mechanism 112R) configured to change the distance between the left and right optometry units.

With this configuration, the distance between the left and right optometry units can be adjusted by the second mechanism according to the interpupillary distance of the subject.

Further, in the optometric apparatus of the embodiment, the movement mechanism system may include a third mechanism (e.g., the vertical movement mechanism 111) configured to vertically move the left and right optometry units.

With this configuration, the positions of the left and right optometry units in the height direction (vertical direction) can be adjusted according to the position of the subject's eyes.

Further, in the optometric apparatus of the embodiment, the movement mechanism system may include a fourth mechanism (e.g., the arm movement mechanism 7) configured to integrally rotate the left and right optometry units.

With this configuration, the left and right optometry units can be retracted from a predetermined examination space by the rotation.

The optometric apparatus of the embodiment may further include the arm (e.g., the horizontal arm 6) and an arm vertical movement mechanism (e.g., the arm movement mechanism 7) configured to vertically move the arm.

With this configuration, the left and right optometry units can be retracted from a predetermined examination space by the movement in the vertical direction.

The optometric apparatus of the embodiment may further include an arm (e.g., the horizontal arm 6) and an arm extending and contracting mechanism configured to extend and contract the arm in the vertical direction (e.g., the arm movement mechanism 7).

With this configuration, the left and right optometry units can be retracted from a predetermined examination space by the movement in the vertical direction caused by the extension and contraction.

Further, the optometric apparatus of the embodiment may further include a controller (e.g., the control device 200) configured to control the movement mechanism system and the left and right optometry units.

With this configuration, subjective measurement and objective measurement can be automatically performed while the examiner is observing the expression of the subject and the like. Also, space saving can be achieved.

Further, the optometric apparatus of the embodiment may further include an arithmetic unit (e.g., the arithmetic unit 210) configured to obtain an objective value based on a measurement result obtained by the objective measurement part.

With this configuration, an objective value obtained by an objective measurement can be used automatically in a subjective measurement.

<Modification>

Note that the configuration of the optical systems described in connection with FIGS. 3 to 5 as well as the configuration and control contents of the control system described in connection with FIG. 6 in the above embodiment are not limitations. For example, the objective measurement may include an objective measurement for obtaining a value related to the subject's eye and photography for capturing an image of the subject's eye. Examples of the objective measurement include objective refraction measurement, corneal shape measurement, tonometry, fundus photography, optical coherence tomography (OCT) measurement using OCT technique, and the like. In addition, examples of the subjective measurement include subjective refraction measurement such as far vision test, near vision test, contrast test, glare test, and the like, and visual field test.

Further, the optometric apparatus of the embodiment can perform far vision test, near vision test, contrast test, glare test, and the like as the subjective measurement. The optometric apparatus can also perform objective refraction measurement, corneal shape measurement, OCT measurement, and the like as the objective measurement. In the OCT measurement, ocular information that indicates the structure of the subject's eye may be obtained. Examples of the ocular information include ocular axial length, thickness of a cornea, anterior chamber depth, thickness of a crystalline lens, and the like.

The embodiments described above are mere examples for embodying or carrying out the present invention, and therefore susceptible to several modifications and variations (omission, substitution, addition, etc.), all coming within the scope of the invention.

While certain embodiments have been described, these embodiments have been presented by way of example only, and are not intended to limit the scope of the inventions. Indeed, the novel embodiments described herein may be embodied in a variety of other forms; further, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An optometric apparatus, comprising:
   a movement mechanism system suspended from an arm; and
   left and right optometry units configured to be moved by the movement mechanism system,
   wherein the left and right optometry units each include
      an optical element applying part configured to selectively apply a plurality of optical elements to a subject's eye,
      a target presenting part configured to selectively present a plurality of visual targets to the subject's eye, and
      an objective measurement part configured for performing objective refraction measurement of the subject's eye.

2. The optometric apparatus of claim 1, wherein the movement mechanism includes a first mechanism configured to relatively change orientations of the left and right optometry units.

3. The optometric apparatus of claim 1, wherein the movement mechanism system includes a second mechanism configured to change a distance between the left and right optometry units.

4. The optometric apparatus of claim 1, wherein the movement mechanism system includes a third mechanism configured to vertically move the left and right optometry units.

5. The optometric apparatus of claim 1, wherein the movement mechanism system includes a fourth mechanism configured to integrally rotate the left and right optometry units.

6. The optometric apparatus of claim 1, further comprising:
   the arm; and
   an arm vertical movement mechanism configured to vertically move the arm.

7. The optometric apparatus of claim 1, further comprising:
   the arm; and
   an arm extending and contracting mechanism configured to extend and contract the arm in a vertical direction.

8. The optometric apparatus of claim 1, further comprising a controller configured to control the movement mechanism system and the left and right optometry units.

9. The optometric apparatus of claim 1, further comprising an arithmetic unit configured to obtain an objective value based on a measurement result obtained by the objective measurement part.

* * * * *